United States Patent [19]

Ward et al.

[11] Patent Number: 4,670,432
[45] Date of Patent: Jun. 2, 1987

[54] PYRAZOLOPYRIDINE DERIVATIVES USEFUL IN TREATING INFLAMMATION AND ALLERGIC CONDITIONS

[75] Inventors: Robert W. Ward; Roger E. Markwell, both of Essex, England

[73] Assignee: Beecham Group p.l.c., Brentford, England

[21] Appl. No.: 852,152

[22] Filed: Apr. 15, 1986

Related U.S. Application Data

[63] Continuation-in-part of Ser. No. 704,611, Feb. 22, 1985, abandoned.

[30] Foreign Application Priority Data

| | | | |
|---|---|---|---|
| Feb. 22, 1984 | [GB] | United Kingdom | 8404584 |
| Feb. 13, 1985 | [EP] | European Pat. Off. | 85101566.9 |
| Feb. 20, 1985 | [AU] | Australia | 38972/85 |
| Feb. 20, 1985 | [CA] | Canada | 474776 |
| Feb. 20, 1985 | [GR] | Greece | 850441 |
| Feb. 20, 1985 | [IE] | Ireland | 420/85 |
| Feb. 20, 1985 | [JP] | Japan | 60-31699 |
| Feb. 20, 1985 | [NZ] | New Zealand | 211166 |
| Feb. 20, 1985 | [ZA] | South Africa | 85/1281 |
| Feb. 21, 1985 | [MX] | Mexico | 11459 |
| Feb. 21, 1985 | [ES] | Spain | 540.609 |
| Jul. 10, 1985 | [AT] | Austria | 2047/85 |
| Jul. 11, 1985 | [DK] | Denmark | 3182/85 |
| Aug. 23, 1985 | [PT] | Portugal | 81.011 |
| Feb. 26, 1986 | [GB] | United Kingdom | 8604698 |

[51] Int. Cl.⁴ .................... A61K 31/44; C07D 471/04
[52] U.S. Cl. .................... 514/210; 514/212; 514/303; 540/597; 546/119; 548/950
[58] Field of Search ........ 546/119; 540/597; 548/950; 514/210, 212, 303

[56] References Cited

U.S. PATENT DOCUMENTS 4,559,348 12/1985 Hurst et al. .................... 546/119

*Primary Examiner*—Henry R. Jiles
*Assistant Examiner*—Bernard I. Dentz
*Attorney, Agent, or Firm*—James F. Haley, Jr.; Paul H. Ginsburg; David K. Barr

[57] ABSTRACT

A compound of formula (I) or a salt thereof:

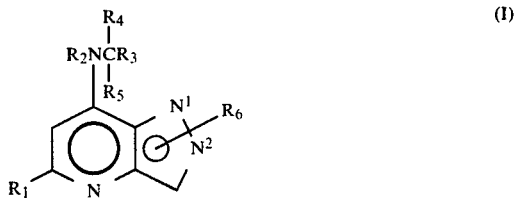

wherein:
$R_1$ is hydrogen, $C_{1-6}$ alkyl or phenyl optionally substituted by halogen, $CF_3$, $C_{1-4}$ alkoxy or $C_{1-4}$ alkyl;
$R_2$ is hydrogen or $C_{1-6}$ alkyl;
$R_3$ is $C_{2-10}$ alkenyl or $C_{1-10}$ alkyl substituted by hydroxy, $C_{1-4}$ alkoxy, thiol, $C_{1-4}$ alkylthio or $NR_7R_8$ wherein $R_7$ and $R_8$ are independently hydrogen or $C_{1-6}$ alkyl or together are $C_{3-6}$ polymethylene;
$R_4$ and $R_5$ are independently hydrogen or $C_{1-4}$ alkyl; and
$R_6$ is hydrogen; or $C_{1-4}$ alkyl or benzyl attached at nitrogen atom 1 or 2;
having anti-inflammatory and/or anti-allergy activity.

20 Claims, No Drawings

PYRAZOLOPYRIDINE DERIVATIVES USEFUL IN TREATING INFLAMMATION AND ALLERGIC CONDITIONS

This application is a continuation-in-part of application Ser. No. 704,611, filed Feb. 22, 1985 and entitled "Pyrazolopyridine Derivatives" now abandoned.

The present invention relates to pyrazolopyridines having useful pharmacological activity, to a process for their preparation and to their use as anti-inflammatories.

J. Heterocycl. Chem. 1971, 8(6), 1035-7 discloses compounds of the formula (A):

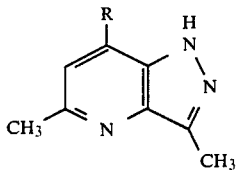

wherein R is $NH_2$, OH, $NAc_2$ or Cl. The compound wherein R is $NAc_2$ is described as having CNS antidepressant activity in mice.

A structurally distinct group of pyrazolopyridine derivatives have now been discovered which compounds have anti-inflammatory (including anti-rheumatic) and/or anti-allergy activity.

Accordingly, the present invention provides a compound of the formula (I):

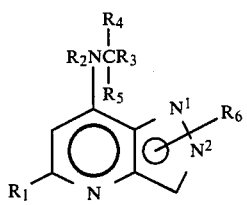

wherein:

$R_1$ is hydrogen, $C_{1-6}$ alkyl or phenyl optionally substituted by halogen, $CF_3$, $C_{1-4}$ alkoxy or $C_{1-4}$ alkyl;

$R_2$ is hydrogen or $C_{1-6}$ alkyl;

$R_3$ is $C_{2-10}$ alkenyl or $C_{1-10}$ alkyl substituted by hydroxy, $C_{1-4}$ alkoxy, thiol, $C_{1-4}$ alkylthio or $NR_7R_8$ wherein $R_7$ and $R_8$ are independently hydrogen or $C_{1-6}$ alkyl or together are $C_{3-6}$ polymethylene;

$R_4$ and $R_5$ are independently hydrogen or $C_{1-4}$ alkyl; and $R_6$ is hydrogen; or $C_{1-4}$ alkyl or benzyl attached at nitrogen atom 1 or 2.

Suitable values for $R_1$ include hydrogen, methyl, ethyl, n- and iso-propyl and phenyl. Preferably $R_1$ is hydrogen or methyl.

Suitable values for $R_2$ include hydrogen, methyl, ethyl, n- and iso-propyl. Favourably $R_2$ is hydrogen.

Suitable values for $R_3$ include vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; $(CH_2)_nCH_3$ wherein n is 0 to 3, substituted by hydroxy, methoxy, ethoxy, n- or iso-propoxy, thiol, methylthio, ethylthio, n- or iso-propylthio or amino optionally substituted by one or two methyl groups or by $C_4$ or $C_5$ polymethylene.

Suitable values for $R_4$ and $R_5$ include hydrogen, methyl and ethyl. Preferably $R_4$ and $R_5$ are both hydrogen.

Suitable values for $R_6$ include hydrogen, methyl, ethyl, n- and iso-propyl and benzyl. More suitably $R_6$ is hydrogen or 2-methyl. Favourably $R_6$ is hydrogen.

It will be appreciated that when $R_6$ is hydrogen the compounds of formula (I) exist as tautomers, i.e. the $R_6$ hydrogen atom is labile. The compounds wherein $R_6$ is hydrogen are therefore of formulae (IIa) and (IIb).

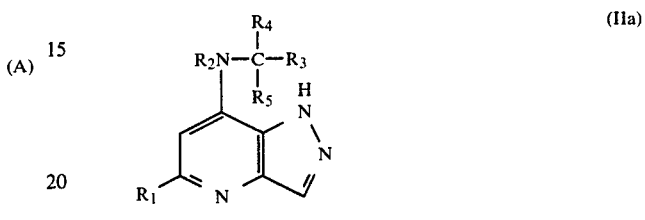

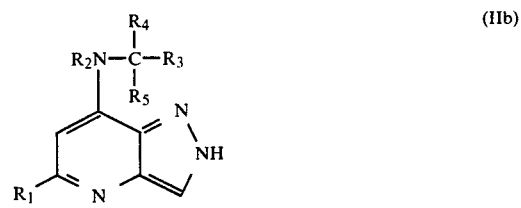

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic. Such salts form on aspect of this invention.

Where compounds of formula (I) form solvates, such as hydrates, these also form an aspect of the invention. Wherever compounds of formula (I) or pharmaceutically acceptable salts are referred to herein, it should be understood, unless indicated otherwise, that solvates, such as hydrates, are included.

There is a group of compounds within formula (I) wherein $R_4$ and $R_5$ are both hydrogen, $R_6$ when other than hydrogen is attached at nitrogen atom 2 and the remaining variables are as defined in formula (I).

There is a favourable group of compounds within formula (I) of formula (III):

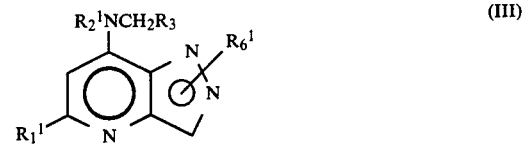

wherein $R_1{}^1$ is hydrogen or methyl, $R_2{}^1$ is hydrogen or methyl, $R_6{}^1$ is hydrogen or 2-methyl, and $R^3$ is as defined in formula (I).

Suitable and preferred values for $R_2{}^1$, $R_6{}^1$ and $R_3$ are as described for the relevant variables under formula (I).

A favourable sub-group of cmpounds within formula (III) is of formula (IV):

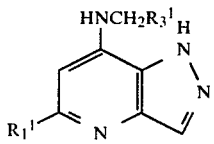

wherein $CH_2R_3^1$ is allyl, 2-methylallyl, 3-hydroxypropyl 2-hydroxyethyl, 2-thiolethyl, 2-methoxyethyl, 2-dimethylaminoethyl, 3-dimethylaminopropyl, 2-pyrrolidinoethyl or 3-pyrrolidinopropyl and $R_1^1$ is as defined in formula (III).

The compounds of this invention are preferably provided in pharmaceutically acceptable and/or substantially pure form.

The present invention also provides a process for the preparation of a compound of formula (I) or a salt or solvate thereof, which process comprises the reaction of a compound of formula (V):

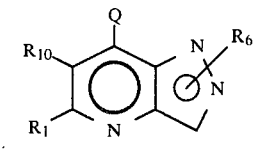

wherein Q is a leaving group, $R_{10}$ is hydrogen, carboxyl or protected carboxyl and $R_1$ and $R_6$ are as defined in formula (I), with a compound of formula (VI):

$HNR_2'R_9$  (VI)

wherein $R_2'$ is $R_2$ or a group or atom convertible thereto and $R_9$ is $CR_3R_4R_5$ or a group or atom convertible thereto; and thereafter converting $R_{10}$ when carboxy or protected carboxy to hydrogen, optionally converting $R_2'$ to $R_2$, $R_9$ to $CR_3R_4R_5$ and/or an $R_6$ hydrogen to an $R_6$ $C_{1-6}$ alkyl group and/or forming a salt and/or solvate thereof.

Preferably salts and/or solvates are obtained in pharmaceutically acceptable form. However salts and solvates which are not pharmaceutically acceptable may be useful as intermediates in the preparation of pharmaceutically acceptable compounds of this invention. Thus non-pharmaceutically acceptable salts and solvates also form an aspect of this invention.

Suitable leaving groups Q include halogens such as chloro and bromo, preferably chloro.

The reaction may be carried out under conventional conditions for nucleophilic aromatic displacements, at elevated temperatures using excess of reagent as solvent or in an inert solvent such as toluene, ethanol, dimethylformamide, dimethylsulphoxide, dioxan or water. If the amine boils at a low temperature it will be appreciated that the reaction preferably takes place in a sealed tube.

In order to prevent unwanted alkylation of an $R_6$ hydrogen atom, it may need to be protected using a protecting group suitable for NH-heteroaromatic functions.

$R_{10}$ is often carboxy or protected carboxy when $R_1$ is hydrogen. Suitable values for protected carboxy include $C_{1-4}$ alkyl esters such as the ethyl ester. Conversion of $R_{10}$ esterified carboxy to $R_{10}$ carboxy is carried out by conventional, usually alkaline, hydrolysis. $R_{10}$ carboxy is then converted to $R_{10}$ hydrogen by decarboxylation by conventional methods such as heating in a high boiling inert solvent e.g. Dowtherm.

Conversion of an $R_2$ hydrogen to an $R_2$ $C_{1-6}$ alkyl group may be carried out by conventional amine alkylation or acylation (e.g. formylation) followed by reduction.

$R_9$ will often be $CR_3R_4R_5$ but it will be appreciated that, according to the type of $R_3$ group it may be necessary to protect functional groups such as amino or hydroxy during the reaction and subsequently deprotect.

An $R_6$ hydrogen atom may be converted to an $R_6$ $C_{1-4}$alkyl group by conventional alkylation procedures.

It will be appreciated that these conversions may take place in any desired or necessary order.

Pharmaceutically acceptable salts of the compounds of formula (I) may be formed conventionally by reaction with the appropriate acid.

Compounds of the formula (V) are either known compounds or can be prepared by analogy with processes for preparing structurally similar known compounds.

For example, compounds of the formula (V) wherein Q is chloro may be prepared by the phosphorus oxychloride chlorination of a compound of formula (VII):

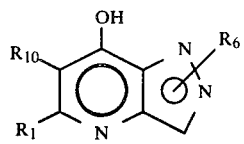

wherein $R_1$, $R_6$ and $R_{10}$ are as defined in formulae (I) and (V).

Compounds of the formula (VII) may be prepared as described in J. Chem. Soc. Perkin Trans. I, 1976 (5), 507 or by analogous methods thereto.

It will be appreciated that the compounds of formula (VII) wherein $R_6$ is hydrogen exist in the predominant tautomeric form of formula (VIIa):

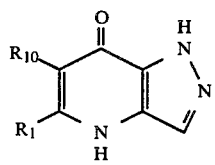

The compounds of this invention find utility in the treatment of inflammatory (including rheumatic) and/or allergic conditions.

Accordingly, in a further aspect the invention provides a pharmaceutical composition for treatment of the above disorders which comprises an effective amount of a compound of formula (I) or a pharmaceutically acceptable or solvate salt thereof and a pharmaceutically acceptable carrier.

The compositions may be adapted for administration via the topical, oral, vaginal, rectal or injection routes.

The compositions of this invention may contain diluents, binder, fillers, disintegrants, flavouring agents, colouring agents, lubricants, preservatives in conventional manner. These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore will normally be made up into a formulation for topical administration to the skin comprising a compound of the invention together with a suitable topically effective vehicle.

Cream, lotion, ointment, liniment, gel, topical solution, gel stick, douche, wash, spray and aerosol formulations that may be used for topical application of compounds of the formula (I) are conventional formulations well known in the art, for example, as described in standard text books of pharmaceutics and cosmetics, such as Harry's Cosmeticology published by Leonard Hill Books, Remingtons Pharmaceutical Sciences published by Mack Publishing Co. and the British and U.S. Pharmacopoeias. A standard emulsifying ointment base or glycerol or anhydrous polyethylene glycol are simple examples of suitable vehicles. Aqueous solutions may be used as vaginal douches or washes for mouth or throat.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, perfumes and alcohol. Advantageously, a penetrating agent such as AZONE may also be included.

The compositions for topical treatment may also contain other thereapeutic agents such as anti-infective and/or anti-viral agents. Suitable anti-infective agents include the topically applicable antibacterial, anti-yeast, anti-fungal and anti-herpes agents.

These compositions may be used in the topical treatment of atopic and contact dermatitis, psoriases, acne, eczema and other inflammatory dermatoses and inflammatory conditions for example lesions of eyes, ears, nose, throat, vagina and rectum, particularly the mucosal membranes. Treatment of inflammation of the skin and mucosal membranes may, however, also be carried out utilising an oral composition of the invention, as hereinbefore described.

It will be appreciated that the amount of the compound of the invention used will depend on a number of factors such as the nature and severity of the disorder being treated, and the specific compound being used. However, by way of illustration it is believed that effective therapy can be achieved using roughly similar amounts of the compounds of the invention as would be used of hydrocortisone. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of prophylaxis of bronchial asthma, rhinitis, hay fever and allergic eczema.

Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 20 to 3000 mg and more usually in the range 40 to 1000 mg. Alternatively the unit dose may contain from 2–20 mg of active agent and may be administered in multiples if desired to give the preceeding daily dose.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

No adverse toxicological effects are indicated at any of the aforementioned dosage ranges.

Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of an effective amount of a compound of formula (I) or a pharmaceutically acceptable salt or solvate thereof to the sufferer.

Mammals which may be thus treated include humans and domestic animals such as dogs, cats or horses.

Most suitably the medicament will be administered as 1, 2, 3 or 4 doses per day at the dose levels previously indicated.

The following Examples illustrate the invention; the following Descriptions illustrate the preparation of intermediates thereto; the following Pharmacological Data illustrates the utility of the invention.

DESCRIPTION 1

4-nitropyrazole (D1)

Pyrazole (20 g) was dissolved in concentrated sulphuric acid (150 cm$^3$). The solution was kept below 10° C. and stirred whilst a mixture of concentrated sulphuric acid (120 cm$^3$) and concentrated nitric acid (120 cm$^3$) was added dropwise. After addition of the acid the solution was gradually heated to a temperature of 120° C. and maintained at this temperature for 24 h, cooled, added to ice, basified with 20% w/v sodium carbonate, 33% w/v, ammonia and 50% w/v sodium hydroxide. The solution was extracted with ether to yield the crude product.

Crystallisation from ethyl acetate (24 g, 66%) gave white plates m.p. 166°–168° C. $\nu$max, 3180, 3130 (both sharp, medium intensity, N—H stretch), 1580, 1540, 1500, 1410, 1290, 995, 940, 815 and 756 cm$^{-1}$.

DESCRIPTION 2

Ethyl 3-(pyrazol-4-ylamino)crotonate ([1]) (D2)

4-Nitropyrazole (D1) (1.13 g), 10% palladium-charcoal (0.14 g), and methanol (40 cm$^3$) were shaken with hydrogen at 5 atm for 3 h. Filtration and evaporation yielded the crude 4-aminopyrazole which was treated with ethyl acetoacetate (1.43 g) and concentrated hydrochloric acid (0.2 cm$^3$). The mixture was heated on a steam bath for 5 min. to yield an oily solid. Trituration with aqueous ethanol gave the crotonate (1.31 g, 67%). Crystallisation from benzene-cyclohexane gave needles, m.p. 119°–120° C. $\nu$max 3400–2500 (N—H), 1650 (C=O), 1620, 1260 (C—O), and 1160 cm$^{-1}$. (1) Foster and Hurst, J.Chem.Soc., Perkin I, p 511 (1976).

DESCRIPTION 3

1,4-dihydro-5-methylpyrazolo 4,3-b Pyridin-7-one ([1]) (D3)

Ethyl 3-(pyrazol-4-ylamino)crotonate (D2) (1.5 g) was added to boiling Dowtherm A (75 cm$^3$). The mixture was heated under reflux for 15 min. allowed to cool, and on dilution with light petroleum (b.p. 60°–80° C.) gave the pyrazolopyridone (0.78 g, 68%). The pyrazolopyridone was washed thoroughly with boiling light petroleum and crystallised from aqueous ethanol (charcoal) to give prisms, mp 330° C.

m+149.0591.

$\nu$max. 3500–2500 (N—H), 1605 (C=O), 1555, 1520, 1415 1265 and 945 cm$^{-1}$.

$\gamma$(CF$_3$—COOH) 1.43 (1H, s, 3—H), 2.78 (1H, s, 6—H) and 7.10 (3H, s, CH$_3$).

(1) Foster and Hurst, J.Chem.Soc., Perkin I. p 511 (1976)

DESCRIPTION 4

7-chloro-5-methyl-1H-pyrazolo(4,3-b)pyridine (D4)

1,4-Dihydro-5-methylpyrazolo[4,3-b]pyridine-7-one (D3) (5 g) was dried and refluxed in phosphorus oxychloride (30 ml), in dry apparatus, for 3 h. Evaporation of the solvent, followed by neutralisation with 10% w/v sodium carbonate solution gave a grey suspension. Filtration gave the chloro-compound (5 g, 89%). Sublimation (0.1 mm Hg, 120° C.) and crystallisation from ethyl acetate-ethanol (charcoal) gave white amorphous crystals m.p. 218°.

$\nu$max. 3250–3000 (broad, N—H stretch), 1560 (N—H, bend), 1310, 1280, 1160, 940, 880, 850, 825 and 758 cm$^{-1}$.

$\delta$(CF$_3$COOH) 2.99 (3H, s, 5—CH$_3$), 7.74 (1H, s, 6—H) and 8.51 (1H, s, 3—H). Total proton count 5.

Found: C, 49.89; H, 3.69; N, 25.27. C$_7$H$_6$N$_3$Cl requires C 50.16; H, 3.62; N, 25.08; Cl 21.18%.

DESCRIPTION 5

7-chloro-1,5-dimethyl-1H-pyrazolo(4,3-b)pyridine (D5a) and
7-chloro-2,5-dimethyl-2H-pyrazolo(4,3-b)pyridine (D5b)

A solution of methyl iodide (9.4 g) in ether (20 ml) was added to a boiling suspension of 7-chloro-5-methyl-1H-pyrazolo(4,3-b)pyridine (D4) (10 g) and sodium hydroxide (3.58 g) in 90% aqueous ethanol (20 ml) and the mixture was heated uner reflux for 3 h. The solvent was removed in vacuo and the residue was extracted with boiling chloroform. The extract was dried (MgSO$_4$) and the solvent removed to give a mixture of the 1-methyl and 2-methyl compounds (11 g). The mixture (5.5 g) was separated by flash column chromatography using a column of 50 mm diameter, a 10″ length of silica, and ethyl acetate as eluant; 50 ml fractions were collected. Fractions 8 to 24 gave the 1-methyl compound (3.45 g, 64%) which was sublimed (0.1 mm Hg, 120°) and then crystallised from ethyl acetate to yield white prisms, m.p. 119°–121°.

$\nu_{max}$ (MeOH) 276 (log $\epsilon$3.74) and 304 nm (3.71), $\nu_{max}$ 1540, 1500, 1340, 1245, 1105, 990, 890, 875, 825, cm$^{-1}$; $\delta$(CF$_3$COOH) 3.08 (3H, s, 5—CH$_3$), 4.68 (3H, s 1—CH$_3$), 7.96 (1H, s 6—H), 8.65 (1H, s, 3—H), total proton count 8.

Found: C, 52.9; H, 4.6; N, 23.1; Cl, 19.8, C$_8$H$_8$N$_3$Cl, Requires: C, 52.9; H, 4.45; N, 23.1; Cl, 19.5%. Fractions 25–37 gave no product. The column was stripped with methanol to yield the 2-methyl compound (1.75 g, 32%) which was sublimed (0.1 mm Hg, 120°) and crystallised from ethyl acetate to yield white needles, m.p. 135°–136°.

$\lambda_{max}$ (MeoH), 285 (log $\epsilon$4.49) and 307 nm (3.73).

$\nu_{max}$ 3100, 1535, 1180, 990, 900, 860, 850, 815, 760, 655 cm$^{-1}$.

$\delta$(CF$_3$COOH) 3.05 (3H, s, 5—CH$_3$), 4.57 (3H, s, 2—CH$_3$), 7.86 (1H, s, 6—H), 8.70 (1H, s, 3—H), total proton count 8.

Found: C, 52.8; H, 4.6; N, 22.9; Cl, 19.5; C$_8$H$_8$N$_3$Cl. Requires: C, 52.9; H, 4.45; N, 23.1; Cl, 19.5%.

DESCRIPTION 6

4,7-Dihydro-7-oxo-1H-pyrazolo[4,3-b]pyridine-6-carboxylic acid (D6)

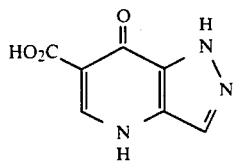

A mixture of ethyl 4,7-dihydro-7-oxo-1H-pyrazolo[4,3-b]pyridine-6-carboxylate[1] (9.0 g, 43.5 mmol) and sodium hydroxide (3.65 g, 91 mmol) in water (60 ml) and methanol (5 ml) was heated under reflux for 90 min, then cooled, diluted with water (70 ml) and adjusted to pH6 with 5N hydrochloric acid. The precipitated solid was collected, washed with water and dried to give the title compound as an off-white solid (7.0 g, 90%) m.p. >330° C. (sublimes).

[1] H. E. Foster and J Hurst, J. Chem. Soc., Perkin Trans. 1, 1976, 507.

DESCRIPTION 7

4,7-dihydro-7-oxo-1H-pyrazolo[4,3-b]pyridine (D7)

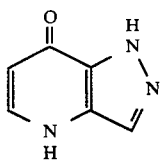

4,7-Dihydro-7-oxo-1H-pyrazolo[4,3-b]pyridine-6-carboxylic acid (D6) (7.0 g, 39 mmol) was suspended in Dowtherm A (250 ml) and the mixture was heated under reflux under nitrogen for 2.5 h. After cooling, the mixture was diluted with 60°-80° petrol and filtered. The precipitate was washed well with petrol and dried to give the crude product as an off-white solid (3.9 g, 74%). Recrystallisation from aqueous ethanol/ether gave the title compound as very fine needles, m.p. >320° C.

$\delta$(DMSO-d$_6$): 6.0 (1H, d, J=7 Hz); 7.75 (1H, d, J=7 Hz); 7.85 (1H, s); 11.85 (1H, bs); 13.60 (1H, bs);

$\lambda_{max}$ MeOH: 298 and 307 nm.

DESCRIPTION 8

7-chloro-1H-pyrazolo[4,3-b]pyridine (D8)

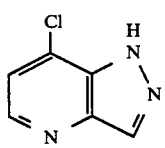

A solution of 4,7-dihydro-7-oxo-1H-pyrazolo[4,3-b]pyridine (D7) (2.0 g, 14.8 mmol) in phosphorus oxychloride (20 ml) was heated under reflux for 90 min. The reagent was removed in vacuo, and the residue was made slightly basic with saturated sodium hydrogen carbonate, and filtered to give a green solid. The solid was extracted with boiling ethyl acetate (2×150 ml), and the solvent was evaporated to leave the chloride as a white solid (1.55 g, 68%), m.p. >320° C.

$\delta$(DMSO-d$_6$): 7.55 (1H, d, J=5 Hz); 8.45 (1H, s); 8.47 (1H, d, J=5 Hz).

$\lambda_{max}$ (MeOH): 291 nm.

DESCRIPTION 9

Ethyl 7-chloro-1H-pyrazolo[4,3-b]pyridine-6-carboxylate (D9)

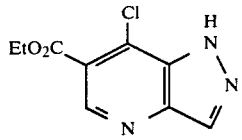

A solution of ethyl 4,7-dihydro-7-oxo-1H-pyrazolo[4,3-b]pyridine-6-carboxylate[1] in phosphorus oxychloride was heated under reflux for 45 min. After removing excess reagent in vacuo, the residue was made basic with saturated sodium hydrogen carbonate solution. The precipitated solid was washed with water, then extracted with ethyl acetate to give the crude title compound.

[1]. H. E. Foster and J. Hurst, J. Chem.Soc., Perkin Trans. 1, 1976, 507

$\delta$(DMSO d$_6$) 1.4 (3H,t,J=7 Hz); 4.3 (2H,q,J=7 Hz); 8.4 (1H,s); 8.8 (1H,s).

A much improved yield (67%) of the title compound was obtained by maintaining the reaction mixture at 70°-80° C. rather than at reflux temperature.

DESCRIPTION 10

Ethyl 7-Allylamino-1H-pyrazolo[4,3-b]-pyridine-6-carboxylate (D10)

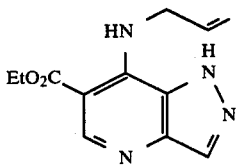

Ethyl 7-chloro-1H pyrazolo[4,3-b]pyridine-6-carboxylate (D9) (2.25 g, 0.01 mole) and allylamine (20 ml) were stirred together overnight at room temperature. The excess allylamine was removed under reduced pressure. The residue was dissolved in the minimum volume of aqueous ethanol and sufficient 10% sodium carbonate added to give pH 8.

The resulting solid was collected and dried to give a yellow solid, which was recrystallized from ether-pentane with a few drops of methanol to facilitate solubility, to give the title compound as the free base (1.0 g, 42%) m.p. 218°-222° C. (Found: C, 58.32; H, 5.72; N, 22.85 C$_{12}$H$_{14}$N$_4$O$_2$ requires C, 58.53; H, 5.73; N, 22.75%)

$\delta$(CDCl$_3$) 1.4 (3H, t, J=7 Hz); 4.3 (2H, q, J=7 Hz); 4.7-4.85 (2H,m); 5.0-5.5 (2H,m); 5.75-6.41 (1H,m); 8.15 (1H,s); 8.8 (1H,s).

EXAMPLE 1

7-Allylamino-5-methyl-1H-pyrazolo[4,3-b]pyridine (E1)

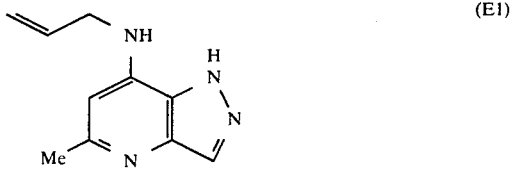
(E1)

A mixture of 7-chloro-5-methyl-1H-pyrazolo[4,3-b]pyridine (D4) (1.0 g, 0.006 mole) and allylamine (60 g) in water (100 ml) was heated under reflux for 12 days. On cooling the reaction mixture was evaporated to dryness, basified to pH8 with 10% sodium carbonate solution and the resulting solid filtered off. Recrystallisation from chloroform/pentane gave the product as white solid (1.0 g). m.p. 172°–174° C.

δ(d$_6$DMSO): 2.40 (3H, s); 3.91 (2H, d, J=6.5 Hz); 3.4–5.0 (1H, br.s exchanges with D$_2$O); 5.00–5.50 (2H, m); 5.68–6.05 (1H, m); 6.15 (1H, s); 6.4–6.7 (1H, br.s exchanges with D$_2$O); 7.85 (1H, s).

Found: C, 63.57; H, 6.35; N, 29.88. C$_{10}$H$_{12}$N$_4$ requires C, 63.81; H, 6.43; N, 29.77%.

EXAMPLE 2

(Method A)

7-[3-hydroxypropylamino]-5-methyl-1H-pyrazolo[4,3-b]pyridine (E2)

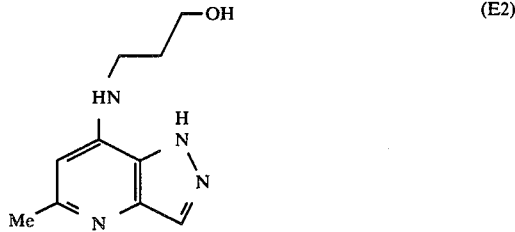
(E2)

7-Chloro-5-methyl-H-pyrazolo[4,3-b]pyridine (D4) (0.5 g, 0.003 mole) and 3-aminopropanol (0.75 g, 0.01 mole) in dry xylene (5 ml) were heated under reflux for 4 h. The solvent was removed under reduced pressure and the resulting oil recrystallised from methanol/ethyl acetate to give the hydrochloride salt of the title compound as a white crystalline solid (398 mg, 55%), m.p. 194°–196° C.

δ(DMSO-d$_6$): 1.80 (2H, quintet, J≈6 Hz); 2.60 (3H, s); 3.25–3.75 (4H, m); 4.60 (1H, br.s); 6.60 (1H, s); 8.20 (1H, s); 9.40 (1H, br.s).

A sample of hydrochloride salt was dissolved in water (10 ml) and brought to pH8 with 10% sodium carbonate. The solution was then freeze-dried to give a white solid which was recrystallised from ethyl acetate/methanol to give the required free base.

Found M+ 206.1166.
Theoretical 206.1167.

Method B (E2)

A quantitative yield of the free base was obtained when the procedure was modified to neutralization of the crude hydrochloride salt directly after removal of the xylene. The required product, probably as a hydrate, crystallised from the aqueous solution on seeding with the previously obtained material. After collection, washing with water and drying the product had initial m.p. at 125° followed by resolidification and final melting at 172°–178°. On drying at >100° only the higher melting point was observed. This latter sample analysed correctly for the free base.

(Found: C,58.04; H,6.89; N,27.60. C$_{10}$H$_{14}$N$_4$O requires C,58.24; H,6.84; N,27.17%).

δ(DMSO-d$_6$) 1.8 (2H,m); 2.4 (3H,s); 3.3 (2H,br.m); 3.55 (2H,br.m); 4.55 (1H,br.t,J=4 Hz); 6.22 (1H,s); 6.3 (1H, br.t,J=4 Hz); 7.92 (1H,s); 12.5 (1H,br.s);

EXAMPLE 3

7-[2-Hydroxyethylamino]-5-methyl-1H-pyrazolo[4,3-b]pyridine (E3)

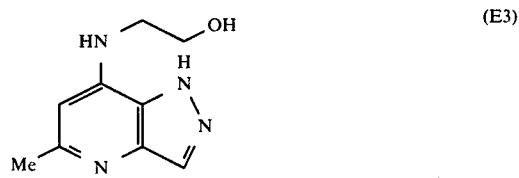
(E3)

The title compound was prepared from 7-chloro-5-methyl-1H-pyrazolo[4,3-6]pyridine (D4) and aminoethanol by Method B used for the preparation of (E2) to give the required product as fine white needles, m.p. initially 112°–115° and resolidification, finally melting at 213°–216°. As in the case of (E2) this hydrated material was dried at >100° C. and then only gave the higher melting point. (Found: C,55.80; H,6.29; N,29.37. C$_9$H$_{12}$N$_4$O$_4$O requires C,56.24; H,6.29; N,29.15%).

δ(DMSO-d$_6$) 2.4 (3H,s); 3.35 (2H, br.m); 3.62 (2H, br.m); 4.85 (1H, br.t,J=4 Hz); 6.23 (1H,s); 6.36 (1H,br.m,J=4 Hz); 7.9 (1H,s); 12.6 (1H,br.s).
Found M+ 192.1015.
C$_9$H$_{12}$N$_4$O requires 192.1011.

The first obtained material with initial m.p. 112°–115° analysed corrected for the hemihydrate of the title compound (Found: C,53.68; H,6.55; N,28.35. C$_9$H$_{12}$N$_4$O.½H$_2$O requires C,53.72; H,6.49; N,27.85%).

EXAMPLE 4

7-[2-Methoxyethylamino-5-methyl-1H-pyrazolo[4,3-b]pyridine (E4)

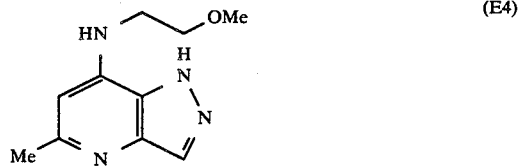
(E4)

7-Chloro-5-methyl-1H-pyrazolo[4,3-b]pyridine (D4) (1 g, 0.06 mole) was heated at reflux under nitrogen in methoxyethylamine for 1 week. Volatile material was removed under vacuum and the residue treated with water (15 ml) and a little methanol. A small amount of insoluble material was filtered off and the filtrate reevaporated to dryness. Chromatography on basic alumina eluting with ethyl acetate with methanol added to a maximum of 15% gave white gum. This was further purified by passing through Dowex 50W column, previously treated with dilute HCl, eluting initially with methanol, then water and finally 5% 0.880 ammonia in water. The fractions containing UV active material were freeze dried giving the title compound as a white solid (0.38 g,31%) m.p. 167°-170° (Found: C, 57.18; H, 6.84; N, 27.06 $C_{10}H_{14}N_4O.0.2H_2O$ requires C,57.23; H, 6.90; N, 26.70%), $\delta$(DMSOd-6) 2.4 (3H,s), 3.2-3.7 (4H,m), 6.25 (1H,s), 6.35 (1H,br.s), 7.9 (1H,s).

Found M+ 206.1173.

$C_{10}H_{14}N_4O$ requires 206.1168.

EXAMPLE 5

7-Allylamino-2,5-dimethyl-pyrazolo[4,3-b]pyridine (E5)

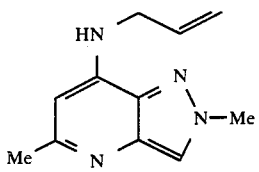

(E5)

7-Chloro-2,5-dimethylpyrazolo[4,3-b]pyridine (D5b) (800 mg, 0.0044 mole) was heated at reflux under nitrogen for 10 days in water (8 ml) and allylamine (8 ml). Volatile material was then removed under reduced pressure, the residue diluted with water (15 ml) and taken to pH 9 with addition of aqueous ammonia. After extraction with ethyl acetate (4×30 ml) the combined organic layers were dried (Na₂SO₄), filtered and evaporated to dryness to give an orange oil (760 mg). This was chromatographed on basic alumina eluting with ethyl acetate to give a total of 518 mg (58%) of material containing the required product, m.p. 84°-90°. Recrystallisation of a sample gave the title compound as pale yellow needles, m.p. 90°-92°, (Found: C, 65.02; H, 6.98; N, 27.74. $C_{11}H_{14}N_4$ required C, 65.32; H, 6.98; N, 27.70), $\delta$(CDCl₃) 2.47 (3H,s), 3.73-4.25 (2H,m), 4.06 (3H,s), 5.0-5.5 (2H,m), 5.63-6.3 (1H,m), 6.0 (1H,s), 7.8 (1H,s).

Found M+ 202.1222.

$C_{11}H_{14}N_4$ requires 202.1218.

EXAMPLE 6

7-[3-Dimethylaminopropylamino]-5-methyl-1H-pyrazolo[4,3-b]pyridine (E6)

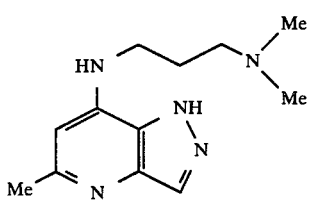

(E6)

The title compound was prepared from 7-chloro-5-methyl-1H-pyrazolo[4,3-b]pyridine (D4) and 3-dimethylaminopropylamine by the method given in Example 2. On neutralization of the thus formed hydrochloride salt a clear solution was produced. After freeze drying, purification was carried out on Dowex 50W as described in Example 4, followed by crystallization from ethyl acetate to give the title compound as a white crystalline solid, m.p. 112°-117°.

$\delta$(DMSO-d₆) 1.55-2.0 (2H,m), 2.23 (3H,s), 2.30-2.55 (2H,m), 3.1-3.5 (2H,m), 6.25 (1H,s), 6.72 (1H,br.t, J=4 Hz), 7.94 (1H,s).

Found M+ 233.1643.

$C_{12}H_{19}N_5$ requires 233.1640.

EXAMPLE 7

7-Allylamino-1H-pyrazolo[4,3-b]pyridine (E7)

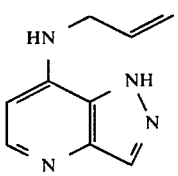

(E7)

Ethyl 7-Allylamino-1H-pyrazolo[4,3-b]pyridine-6-carboxylate (D10) (1.0 g 0.004 mole) was converted to the corresponding acid by heating under reflux with a 2% sodium hydroxide solution in ethanol (50 ml). The ethanol was removed under reduced pressure, and the residue diluted with water (10 ml) and acidified to pH5 with dilute hydrochloric acid. The resulting acid was filtered and dried, m.p. 230°-232° C.

The acid was dissolved in Dowtherm A (50 ml) and heated under reflux for 40 minutes. The reaction mixture was cooled and diluted with a large volume of petroleum ether 60°-80°. The resulting solid was filtered off and recrystallized from ether/methanol to give the title compound (450 mg, 65%) m.p. 115°-118°.

$\delta$(CDCl₃) 3.80-3.95 (2H, m); 4.85-5.29 (2H, m); 5.45-6.0 (1H, m); 6.20 (1H, d, J=5 Hz); 8.05 (1H, s); 8.21 (1H, d, J=5 Hz).

EXAMPLE 8

7-(2-Methylallylamino)-5-methyl-1H-pyrazolo[4,3-b]pyridine (E8)

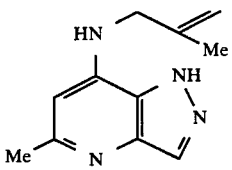

(E8)

The title compound was prepared from 7-chloro-5-methyl-1H-pyrazolo[4,3-b]pyridine (D4) and 2-methylallylamine as a pale yellow solid, m.p. 161°-164°, by the method given in Example 1.

$\delta$(DMSO-d₆) 1.78 (3H,br s); 2.42 (3H,s); 3.87 (2H,br d, J-5 Hz); 4.8-5.1 (2H,m); 6.19 (1H,s); 6.57 (1H, br t); 7.93 (1H,s); 12.58 (1H,br s).

EXAMPLE 9

7-(3-Dimethylaminopropylamino)-5-methyl-1H-pyrazolo[4,3-b]pyridine hydrochloride, monohydrate (E9)

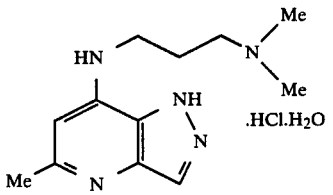

A mixture of 7-chloro-5-methyl-1H-pyrazolo[4,3-b]pyridine (D4) (19.21 g, 0.115 mole) and 3-dimethylaminopropylamine (100 g) in xylene (770 ml) was heated at reflux under nitrogen for 83 h. After allowing to cool to room temperature, volatile material was removed under reduced pressure. The residue, an orange oil, was treated with ether and methanol and then left to stand at 4° C. overnight. The resulting pale yellow crystalline solid was collected, washed with ether/methanol and dried under vacuum to give the title compound (12.5 g, 38%), m.p. 183°–186° C. (Found: C,50.29; H,7.53; N,24.44. $C_{12}H_{19}N_5.HCl.H_2O$ requires: C,50.08; H,7.69; N,24.34%).

δ(DMSO-$d_6$) 1.88–2.05 (2H,m); 2.47 (3H,s); 2.53 (6H,s); 2.82–2.95 (2H,m); 3.32–3.47 (2H,m); 6.37 (1H,s); 7.9 (1H, brs); 8.01 (1H, s);

EXAMPLE 10

7(3-Dimethylaminopropylamino)-5-methyl-1H-pyrazolo[4,3-b]pyridine hemihydrate (E10)

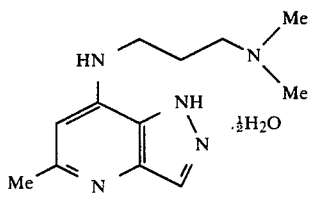

The monohydrochloride monohydrate (E9) was dissolved in water and neutralized with 10% sodium hydroxide solution. After removal of solvent and chromatography on basic alumina with ethyl acetate/methanol as eluant, the anhydrous free base 7-(3-dimethylaminopropylamino-5-methyl-1-H-pyrazolo[4,3-b]pyridine was obtained as a colourless gum. The colourless gum was covered with water and left to stand at 4° C. overnight. The resulting white crystals were collected, washed with water and dried to give the title compound, m.p. 108°–111° C. Water content analysis indicated an average of 0.47 $H_2O$ per molecule of free base.

PHARMACOLOGICAL DATA

Mouse Oxazolone Screen

Compounds were tested for topical anti-inflammatory activity in a screen using the mouse sensitised to oxazolone, by a method modified from that of Dietrich and Hess [Dietrich, F. M., and Hess, R., Int. Arch. Allergy, (1970), 38, 246–259].

Mice were sensitised with oxazolone (2 mg in 20 μl ethanol) on a shaved area of the abdomen. Five days later, the animals received 10 μl THF/MeOH (1:1 v/v) on the right ear, and the test compound in the same solvent on the left ear. One hour later, the animals were challenged with 100 μg oxazolone in 10 μl acetone on each ear. Ear weights were measured 24 h later. Percentage inhibition of the inflammatory swelling refers to the increase in weight of left ears (oxazolone plus compound) compared with solvent-treated negative controls, as a proportion of the increase in weight of right ears (oxazolone alone) over similar controls.

The activity of a selection of compounds of this invention is shown in Table 1.

TABLE 1

| Compound Example No. | Mouse Oxazolone Data % Inhibition | Concentration (μg/ear) |
|---|---|---|
| 1 | 62 | 200 |
| 2 | 82 | 500 |

TABLE 1-continued

| Compound Example No. | Mouse Oxazolone Data % Inhibition | Concentration (μg/ear) |
|---|---|---|
| 3 | 65 | 200 |
| 4 | 52 | 200 |
| 5 | 71 | 200 |

Mouse Cantharidin Screen

Compounds were tested for topical anti-flammatory activity in a cantharidin mouse ear screen, modified from Swingle et al [Swingle, K. F., Reiter, M. J. and Schwartzmiller, D. H., Arch. Int. Pharmacodyn. (1981), 254, 168–176].

25 μg cantharidin (in 10 μl THF/MeOH) was applied to both ears. Compound, in the same solvent, was applied at the same time, to the left ear only. Ears were weighed 24 h after cantharidin application. Percentage inhibition of the acute inflammatory swelling refers to the increase in weight of left ears (catharidin plus compound) compared with solvent-treated negative controls, as a proportion of the increase in weight of right ears (cantharidin alone) over similar controls.

Details of the activity of illustrative compounds of this invention are shown in Table 2.

TABLE 2

| Compound Example No. | Mouse Cantharidin Data (24 h) % Inhibition | Concentration (μg/ear) |
|---|---|---|
| 1 | 88 | 200 |
| 2 | 82 | 200 |
| 3 | 76 | 200 |
| 4 | 57 | 200 |
| 5 | 68 | 200 |
| 6 | 97 | 500 |
| 7 | 83 | 500 |

RBL-1 5-Lipoxygenase Screen

5-Lipoxygenase enzyme was prepared as a 10,000 g supernatant from RBL-1 cells by the method of Jakschik [Jakschik, B. A., Sun, F. F., Lee, L. M. and Steinhoff, M. M., 1980, Biochem. Biophys. Res. Comm. 95, 103]. The 10,000 g supernatant was diluted with homogenization buffer to the equivalent of 1.5–2.5×$10^7$ cells ml$^{-1}$ and made 2 mM with respect to $CaCl_2$. Aliquots of 0.5 ml were then dispensed into tubes, and incubated at 29° C. with 5 γl ethanol or compound in ethanol at the desired concentration for 2 min. Then [1-$^{14}$C] arachidonic acid was added in buffer to give a final concentration of 6.3. μm and 0.2 μCi per incubation, and the reaction continued at 29° C. for 2 min. The reaction was terminated by adding 1 ml of acetone and cooling on ice. 0.5 ml of ice cold saline and 10 μl of 2N formic acid were added, and the mixture was extracted with 2×2 ml of chloroform. The extract was stored under $N_2$ at −20° C. until analysis by chromatography. Activity was measured as the percentage of total radioactivity found in 5-HETE and 5,12-diHETE, and inhibition calculated as the decrease in formation of the sum of these two species in compound-treated incubates relative to control incubates.

In this test the compound of Example 1 gave an inhibition of 39% at 20 μM.

We claim:

1. A compound of formula (I) or a pharmaceutically acceptable salt thereof:

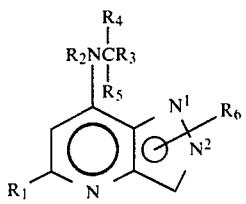
(I)

wherein:
$R_1$ is hydrogen, $C_{1-6}$ alkyl or phenyl optionally substituted by halogen, $CF_3$, $C_{1-4}$ alkoxy or $C_{1-4}$ alkyl;
$R_2$ is hydrogen or $C_{1-6}$ alkyl;
$R_3$ is $C_{2-10}$ alkenyl or $C_{1-10}$ alkyl substituted by hydroxy, $C_{1-4}$ alkoxy, thiol, $C_{1-4}$ alkylthio or $NR_7R_8$ wherein $R_7$ and $R_8$ are independently hydrogen or $C_{1-6}$ alkyl or together are $C_{3-6}$ polymethylene;
$R_4$ and $R_5$ are independently hydrogen or $C_{1-4}$ alkyl; and
$R_6$ is hydrogen; or $C_{1-4}$ alkyl or benzyl attached at nitrogen atom 1 or 2.

2. A compound according to claim 1 of formula (III):

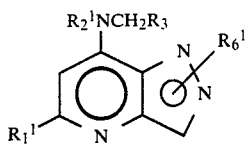
(III)

wherein $R_1^1$ is hydrogen or methyl, $R_2^1$ is hydrogen or methyl, $R_6^1$ is hydrogen or 2-methyl and $R_3$ is as defined in claim 1.

3. A compound according to claim 2 of formula (IV):

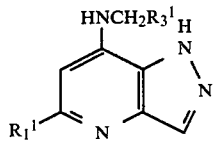
(IV)

wherein $CH_2R_3^1$ is allyl, 2-methylallyl, 3-hydroxypropyl 2-hydroxyethyl, 2-thiolethyl, 2-methoxyethyl, 2-dimethylaminoethyl, 3-dimethylaminopropyl, 2-pyrrolidinoethyl or 3-pyrrolidinopropyl and $R_1^1$ is hydrogen or methyl.

4. A compound according to claim 3 wherein $R_1^1$ is methyl.

5. A compound according to claim 3 wherein $CH_2R_3^1$ is allyl, 2-methylallyl, 3-hydroxypropyl 2-hydroxyethyl, 2-methoxyethyl 2-dimethylaminoethyl or 3-dimethylaminopropyl.

6. A compound according to claim 1 selected from the group consisting of
7-[3-hydroxypropylamino]-5-methyl-1H-pyrazolo[4,3-b]pyridine,
7-[2-hydroxyethylamino]-5-methyl-1H-pyrazolo[4,3-b]pyridine,
7-[2-methoxyethylamino]-5-methyl-1H-pyrazolo[4,3-b]pyridine,
7-allylamino-2,5-dimethyl-pyrazolo[4,3-b]pyridine,
7-allylamino-1H-pyrazolo[4,3-b]pyridine, and
7-(2-methylallylamino)-1H-pyrazolo[4,3-b]pyridine.

7. A compound according to claim 1 which is 7-allylamino-5-methyl-1H-pyrazolo[4,3-b]pyridine.

8. A compound according to claim 1 which is 7-(3-dimethylaminopropylamino)-5-methyl-1H-pyrazolo[4,3-b]pyridine.

9. A compound according to claim 8 as a hydrochloride salt.

10. A compound according to claim 8 as a hydrate.

11. A pharmaceutically acceptable salt according to claim 1.

12. A compound according to claim 11 which is a hydrochloride salt.

13. A compound according to claim 1 as a pharmaceutically acceptable solvate.

14. A compound according to claim 13 which is a hydrate.

15. A pharmaceutical composition for treating inflammatory and/or allergic conditions comprising an effective amount of a compound according to claim 1 or a pharmaceutically acceptable salt thereof and a pharmaceutically acceptable carrier.

16. A composition according to claim 15 in which the compound of a claim 1 or its salt is in hydrated form.

17. A method of treatment or prophylaxis of inflammatory and/or allergic conditions in mammals which comprises the administration of an effective amount of a compound according to claim 1 or a pharmaceutically acceptable salt thereof to the sufferer.

18. A method according to claim 17 in which the compound of claim 1 or its salt is in hydrated form.

19. A pharmaceutical composition for topical treatment of inflammatory conditions comprising a topically effective anti-inflammatory amount of a compound according to claim 1 or a pharmaceutically acceptable salt or solvate thereof together with a pharmaceutically acceptable topically applicable vehicle.

20. A compound according to claim 4 wherein $CH_2R_3^1$ is allyl, 2-methylallyl, 3-hydroxypropyl 2-hydroxyethyl, 2-methoxyethyl 2-dimethylaminoethyl or 3-dimethylaminopropyl.

* * * * *

UNITED STATES PATENT AND TRADEMARK OFFICE
CERTIFICATE OF CORRECTION

PATENT NO. : 4,670,432
DATED : June 2, 1987
INVENTOR(S) : Ward et al.

It is certified that error appears in the above-identified patent and that said Letters Patent is hereby corrected as shown below:

Cover Page   Under "Foreign Application Priority Data", between "Feb. 22, 1984 [GB] United Kingdom...8404584" and "Feb. 26, 1986 [GB] United Kingdom...8604698", delete the remainder of the cited patent applications.

Cover Page   Under "U.S. Patent Documents" insert --4,048,184  9/1977  Hoehn... 260/296--

Cover Page   Under "4,048,184 9/1977 Hoehn.... 260/296" insert --FOREIGN PATENT DOCUMENTS --

Cover Page   Under "Foreign Patent Documents" insert --119774   9/1984   EPO--

Cover Page   Under "119774   9/1984   EPO" insert --Other Documents--

UNITED STATES PATENT AND TRADEMARK OFFICE
CERTIFICATE OF CORRECTION

PATENT NO. : 4,670,432
DATED : June 2, 1987
INVENTOR(S) : Ward et al.

It is certified that error appears in the above-identified patent and that said Letters Patent is hereby corrected as shown below:

Cover Page   Under "Other Documents" insert --E. Ajello, "New Syntheses of Condensed Heterocycles from Isoxazole Derivatives. II. Pyrazolo [4,3-b] Pyridine." J. Heterocycl. Chem. 1971, 8(6), 1035-37.--

--F.M. Dietrich and R. Hess, "Hypersensitivity in Mice." Int. Arch. Allergy 38: 246-259 (1970).--

--H.E. Foster and J. Hurst, "Pyrazolopyridines. Part IV. Preparation and Tautomerism of 6-Cyano-and 6-Ethoxycarbonyl-1,4-dihydropyrazolo [4,3-b] pyridin-T-ones" J. Chem. Soc. - Perkin Transactions I, 1976(5), 507.--

UNITED STATES PATENT AND TRADEMARK OFFICE
CERTIFICATE OF CORRECTION

PATENT NO. : 4,670,432
DATED : June 2, 1987
INVENTOR(S) : Ward et al.

Page 3 of 4

It is certified that error appears in the above-identified patent and that said Letters Patent is hereby corrected as shown below:

--B.A. Jakschik et al., "Calcium Stimulation of a Novel Lipoxygenase," Biochemical and Biophysical Research Communications 95: 103-110 (1980).--

--K.F. Swingle et al., "Comparison of Croton Oil and Cantharidin Induced Inflammations of the Mouse Ear and their Modification by Topically-Applied Drugs," Arch. Int. Pharmacodyn., (1981), 254: 168-176.--

--Chemical Abstracts, 87:168030e November 21, 1977--

Col. 2, line 37, "On" should be --one--

Col. 2, line 61, "$R^3$" should be --$R_3$--

UNITED STATES PATENT AND TRADEMARK OFFICE
CERTIFICATE OF CORRECTION

PATENT NO. : 4,670,432
DATED : June 2, 1987
INVENTOR(S) : Ward et al.

It is certified that error appears in the above-identified patent and that said Letters Patent is hereby corrected as shown below:

Col. 2, line 67, "cmpounds" should be --compounds--

Col. 5, line 63, "of" (first occurrence) should be --or--

Col. 8, line 34, "uner" should be --under--

Col. 8, line 47, "$\nu$" should be --$\lambda$--

Col. 8, line 61, "(MEoH)" should be --(MEOH)--

Col. 12, line 33, "$C_9H_{12}N_4O_4O$" should be --$C_9H_{12}N_4O$--

Col. 12, line 40 "corrected" should be --correctly--

Col. 16, line 12, "anti-flammatory" should be --anti-inflammatory--*

Signed and Sealed this

Twenty-seventh Day of September, 1988

Attest:

DONALD J. QUIGG

Attesting Officer        Commissioner of Patents and Trademarks